United States Patent [19]

Lacefield

[11] 4,074,998

[45] Feb. 21, 1978

[54] METHOD OF CONTROLLING AQUATIC WEEDS

[75] Inventor: William B. Lacefield, Indianapolis, Ind.

[73] Assignee: Eli Lilly and Company, Indianapolis, Ind.

[21] Appl. No.: 783,124

[22] Filed: Mar. 31, 1977

Related U.S. Application Data

[63] Continuation-in-part of Ser. No. 719,308, Aug. 31, 1976, abandoned.

[51] Int. Cl.² ............................................. A01N 9/24
[52] U.S. Cl. ......................................................... 71/66
[58] Field of Search ........................................... 71/66

[56] References Cited

U.S. PATENT DOCUMENTS

| 2,723,193 | 11/1955 | Todd | 71/66 |
|---|---|---|---|
| 3,677,735 | 7/1972 | Richter et al. | 71/66 |
| 3,808,257 | 4/1974 | Richter et al. | 71/66 X |

*Primary Examiner*—Lewis Gotts
*Assistant Examiner*—Catharine L. Mills
*Attorney, Agent, or Firm*—Dwight E. Morrison; Arthur R. Whale

[57] ABSTRACT

A method of controlling aquatic weeds which comprises adding to a body of water containing the aquatic weeds a substituted phenoxy(phenylthio)alkylamine in sufficient quantity to kill the weeds.

9 Claims, No Drawings

METHOD OF CONTROLLING AQUATIC WEEDS

CROSS-REFERENCE

This application is a continuation-in-part of my copending application Ser. No. 719,308, filed Aug. 31, 1976, now abandoned.

BACKGROUND OF THE INVENTION

1. Field of the Invention

The field of the invention relates to the control of aquatic weeds in canals, streams, ponds, lakes and impoundments.

2. Description of the Prior Art

The problems of controlling the growth of organisms in aqueous systems are serious and growing daily more severe. Both submerged and floating aquatic weeds cause major problems in irrigation and water distribution systems. The growth of weeds in irrigation canals greatly reduces the conductivity and capacity of such systems, with resulting substantial economic loss. Large sums are therefore currently being spent in the mechanical and other methods of removal of weed growths from irrigation canals, especially in the southern and western parts of the United States.

Because of the great difficulties involved in the mechanical removal of weeds and other undesired forms of aquatic life from irrigation canals, streams, ponds, lakes, impoundments, etc., it has been proposed to utilize chemical control. Accordingly, various types of chemicals have been added to such bodies of water.

The search for an effective aquatic herbicide continues, since there exists a very distinct need for a method of controlling the growth of aquatic weeds.

In the prior art, Lacefield et al., J. Med. Chem. 14, 133 (1971) teach certain biphenylyloxyalkylamines as useful for inhibiting ADP-induced platelet aggregation in vitro. There is no teaching that the compounds are or would be useful against aquatic weeds. I have found some of the compounds disclosed in this reference to be active against aquatic weeds and such compounds are included within the scope of the present application.

Also in the prior art, Abood et al., Arch. Intern. Pharmacodynamie 134, 106–130 (1961), C.A. 56, 14874h (1962), teach the relation between chemical constitution and biochemical behavior of aryloxyalkylpiperazines, which compounds are alleged to be psychotropic agents. There is no teaching or suggestion in the reference that compounds similar to those disclosed by the reference would be active as aquatic herbicides.

Vernsten et al., J. Am. Chem. Soc. 78, 5398–5400 (1956), C.A. 51, 2794 (1957), teach the preparation of a number of halogen substituted aryl alkamine ethers alleged to possess fungistatic properties. There is no disclosure or teaching in this reference that the compounds disclosed therein would be active as aquatic herbicides.

Another prior art reference is Wright et al., U.S. Pat. No. 2,935,439 (May 3, 1960), which teaches the preparation and fungicidal properties of a number of halogen substituted aminoalkanol aryl ethers. This patent reference does not teach that the compounds disclosed therein, which are similar to those disclosed in the instant application, would be active as aquatic herbicides.

Another prior art reference is British Pat. No. 521,575 (May 24, 1940), also C.A. 36, 783 (1942), which teaches the preparation of a number of aminoalkoxybiphenyl derivatives. There is no teaching in the reference of possible activities of the compounds and therefore no suggestion that similar compounds would be active as aquatic herbicides.

Also in the prior art, Richter et al., U.S. Pat. No. 3,808,257 (Apr. 30, 1974), disclose and claim a series of N-cyanoalkyl-N-cycloalkyl-N-phenoxyalkylamines, alleged to be active as aquatic herbicides. The compounds of this reference are different from the compounds of the present application, and outside the scope of the generic disclosure and claims of the present application.

Still another prior art reference is Richter et al., U.S. Pat. No. 3,677,735 (July 18, 1972), wherein is taught and claimed a method of controlling aquatic plant life using substituted phenoxyalkylamines. The compounds of this Richter et al. reference are outside the scope of the generic disclosure and claims of the present application.

Another prior art reference is Todd, U.S. Pat. No. 2,723,193 (Nov. 8, 1955), which claims a method for the control of terrestrial weeds using a substituted urea bearing a monovalent binuclear aromatic radical and compositions for use in that method. No urea compounds are utilized in the novel method of the present application.

SUMMARY OF THE INVENTION

The present invention relates to a method of controlling aquatic weeds by adding to the water containing such aquatic weeds an herbicidally-effective amount of a substituted phenoxy(phenylthio)alkylamine.

DESCRIPTION OF THE PREFERRED EMBODIMENT

This invention relates to a novel method for the control of aquatic weeds. More particularly, this invention relates to a novel method and compositions for the control of aquatic weeds using a compound of the formula

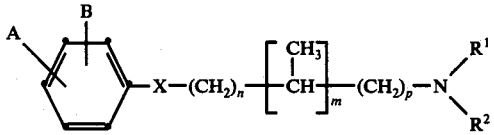

wherein
A is hydrogen, bromo, or chloro;
B is cyclohexyl, benzyl, or phenyl;
X is oxygen or sulfur;
$m$ is 0 or 1;
when $m = 0$, $n + p$ is 2 through 10; and
when $m = 1$, $n = p = 1$, or $n = 2$, $p = 0$;
$R^1$, when taken alone, is hydrogen, $C_1$–$C_5$ alkyl, or —CH$_2$CH$_2$OH;
$R^2$, when taken alone, is hydrogen, $C_1$–$C_5$ alkyl, $C_3$ alkenyl, cyclohexyl, —CH$_2$CH$_2$OH, —(CH$_2$)$_3$OCH$_3$, 1-adamantyl, benzyl, or phenyl;
$R^1$ and $R^2$, when taken together with the nitrogen atom to which they are attached, form morpholino, 2-methylpiperidino, 4-(2-hydroxyethyl)piperazino, or pyrrolidino; and
the acid addition salts thereof.

One embodiment of this invention relates to the use as an aquatic herbicide of a compound of the formula

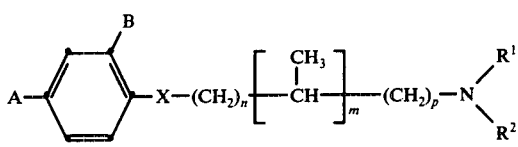

wherein
A is hydrogen, bromo, or chloro;
B is phenyl;
X is oxygen or sulfur;
$m$ is 0 or 1;
when $m = 0$, $n + p$ is 2 through 10; and
when $m = 1$, $n = p = 1$, or $n = 2$, $p = 0$;
$R^1$ is hydrogen, $C_1$-$C_5$ alkyl, or —$CH_2CH_2OH$;
$R^2$ is hydrogen, $C_1$-$C_5$ alkyl, $C_3$ alkenyl, cyclohexyl, —$CH_2CH_2OH$, or —$(CH_2)_3OCH_3$; and
the acid addition salts thereof.

Another embodiment of this invention relates to the use as an aquatic herbicide of a compound of the formula

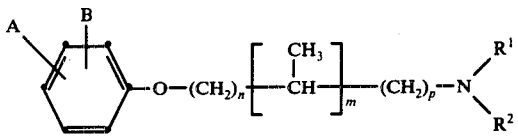

wherein
A is hydrogen or chloro;
B is phenyl;
$m$ is 0 or 1;
when $m = 0$, $n + p$ is 3; and
when $m = 1$, $n = 2$ and $p = 0$;
$R^1$ and $R^2$, taken together with the nitrogen atom to which they are attached, form morpholino, 2-methylpiperidino, 4-(2-hydroxyethyl)piperazino, or pyrrolidino;
and the acid addition salts thereof.

Yet another embodiment of this invention relates to the use as an aquatic herbicide of a compound of the formula

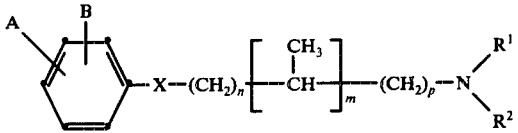

wherein
A is hydrogen;
B is phenyl;
X is oxygen or sulfur;
$m$ is 0 or 1;
when $m = 0$, $n + p$ is 3 or 4; and
when $m = 1$, $n = 2$, and $p = 0$;
$R^1$ and $R^2$ are both methyl; and the acid addition salts thereof.

Still another embodiment of this invention relates to the use as an aquatic herbicide of a compound of the formula

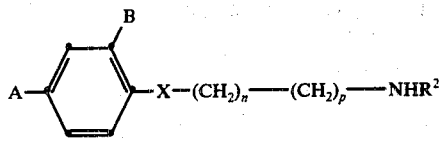

wherein
A is hydrogen or chloro;
B is phenyl;
X is oxygen or sulfur;
$n + p$ is 3, 4, or 5;
$R^2$ is 1-adamantyl; and the acid addition salts thereof.

Another embodiment of this invention relates to the use as an aquatic herbicide of a compound of the formula

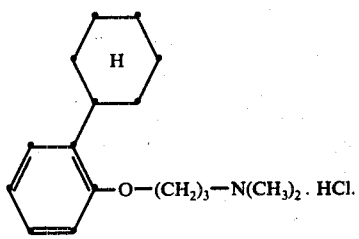

Still another embodiment of this invention relates to the use as an aquatic herbicide of a compound of the formula

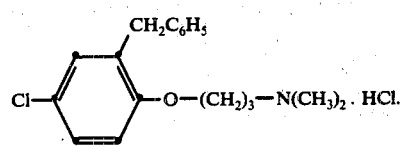

And another embodiment of this invention relates to the use as an aquatic herbicide of a compound of the formula

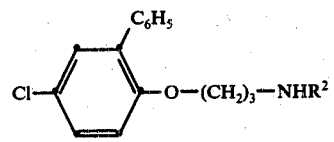

wherein
$R^2$ is phenyl or benzyl; and the acid addition salts thereof.

Compounds preferred for use in the novel method of this invention are of the formula

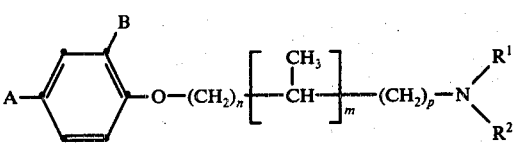

A is chloro;
B is phenyl;
$m$ is 0 or 1;
when $m = 0$, $n + p$ is 2 through 6; and
when $m = 1$, $n = p = 1$, or $n = 2$, and $p = 0$;
$R^1$ is hydrogen, $C_1$-$C_5$ alkyl, or —$CH_2CH_2OH$;

$R^2$ is hydrogen, $C_1$-$C_5$ alkyl, $C_3$ alkenyl, —CH$_2$CH$_2$OH, —(CH$_2$)$_3$OCH$_3$, or cyclohexyl; and the acid addition salts thereof.

Compounds of choice for use in the novel method of this invention are of the formula

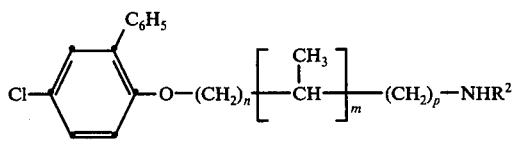

wherein
m is 0 or 1;
when $m = 0$, $n + p$ is 2, 3, or 4;
when $m = 1$, $n = 2$, and $p = 0$;
$R^2$ is $C_2$-$C_4$ alkyl, cyclohexyl, or —(CH$_2$)$_3$OCH$_3$; and
the acid addition salts thereof.

In the above formulae, $C_1$-$C_5$ alkyl represents a saturated straight- or branched-chain hydrocarbon radical such as methyl, ethyl, n-propyl, isopropyl, n-butyl, isobutyl, s-butyl, t-butyl, n-pentyl, 2-pentyl, 3-pentyl, and neopentyl.

$C_3$ Alkenyl represents allyl or prop-1-enyl.

The acid addition salts are prepared from an acid having sufficient acidity to react with the amino moiety of the compound in question. Such acids include hydrochloric, hydrobromic, nitric, sulfuric, oxalic, methanesulfonic, p-toluenesulfonic, and the like. The preparations are carried out following standard preparative methods well known to those skilled in the art.

The compounds useful in the instant novel method and compositions can be prepared by general procedures well known to the art. One procedure involves the reaction of a dialkylaminoalkyl halide with the alkali metal salt of an appropriately substituted phenol in a suitable solvent such as ethanol. In practice, the sodium salt of the substituted phenol is generally used, although other alkali metal salts would be satisfactory, such as the potassium or lithium salts of the substituted phenol. The product is isolated as the free base or as an acid addition salt, as desired, or as dictated by the properties of the desired compound.

Another procedure involves the reaction of a substituted phenoxyalkyl or phenylthioalkyl halide with an appropriate amine at an elevated temperature. The reaction may be carried out by heating the reactants together in a suitable solvent, for example ethanol, followed by isolation of the desired product via distillation or through formation of an acid addition salt of the substituted phenoxy(phenylthio)alkylamine compound.

The preparation may also be carried out by heating the substituted phenoxyalkyl or phenylthioalkyl halide with an excess of the appropriate amine in a sealed stainless steel reaction vessel. The product is isolated from the reaction product mixture as the free base or as the acid addition salt of the substituted phenoxy(phenylthio)alkylamine.

As will be recognized by those skilled in the art, many of the intermediate substituted phenols, dialkylaminoalkyl halides, and amines necessary for the synthesis of the final products usable in the novel method and compositions of this invention, are commercially available.

Those intermediate compounds which are commercially unavailable are synthesized by general methods taught in the literature and familiar to those skilled in the art.

The dialkylaminoalkyl halides are readily prepared by allowing a dialkylaminoalkanol to react with a halogenating agent, such as thionyl chloride, phosphorus oxybromide, or the like, in a suitable solvent, and isolating the desired dialkylaminoalkyl halide as the hydrohalide salt. Such a preparation is more specifically described as follows.

Thus, for example, the dialkylaminoalkyl halide identified as 3-chloro-N,N,1-trimethylpropylamine hydrochloride is prepared following the procedure outlined by Lacefield et al., supra. According to that procedure, 3-dimethylaminobutanol is dissolved in a suitable solvent such as chloroform, the solution cooled, saturated with hydrogen chloride, a solution of thionyl chloride in chloroform is added thereto with stirring and continued cooling. The reaction mixture is allowed to warm to room temperature and to stir overnight, followed by refluxing for a suitable period of time, that is, for about two hours. The reaction product mixture is evaporated to dryness and flushed several times with ethanol. The residue is recrystallized from a suitable solvent such as ethanol-ether to yield product having a melting point of about 144°–146° C. The product is identified by elemental analyses as 3-chloro-N,N,1-trimethylpropylamine hydrochloride.

In some instances the substituted phenols used as intermediates are commercially available. For example, 5-chloro-2-hydroxybiphenyl and 3-chloro-2-hydroxybiphenyl are separated by fractional distillation of a mixture of chlorophenylphenol (chlorohydroxybiphenyl) isomers identified commercially as Dowicide 32.

Another intermediate substituted phenol, namely 2-chloro-5-hydroxybiphenyl, is prepared by the isomerization of 2-hydroxybiphenyl using aluminum chloride according to the procedure of Hay, J. Org. Chem. 30, 3577 (1965), followed by reaction of the desired 3-hydroxybiphenyl with sulfuryl chloride to yield the required 2-chloro-5-hydroxybiphenyl.

Other intermediates needed in the preparation of the final products are the ω-haloalkoxy substituted phenyl compounds, which can be prepared according to the procedure of Lacefield et al., supra. Thus, a solution of 5-chloro-2-hydroxybiphenyl, potassium hydroxide, and 1,10-dibromodecane, in a suitable solvent, such as methanol is allowed to reflux for a period of time, suitably overnight. The reaction product mixture is cooled and filtered, and the filtrate concentrated in vacuo to remove solvent. The crude liquid material remaining is dissolved in ether and washed successively with dilute aqueous sodium hydroxide and water until the washings are neutral. The organic layer is dried over a suitable drying agent, filtered, and distilled in vacuo to yield product having a boiling point of about 230°–235° C./0.1 mm., and identified as 2-(10-bromodecyloxy)-5-chlorobiphenyl.

Other ω-haloalkyl substituted phenyl compounds are prepared in the same general manner. However, in some cases, because of instability of the product to prolonged heating, distillation is stopped after the excess dihaloalkane is removed, and the crude ω-haloalkyl substituted phenyl compound used without further purification.

Alkylaminoalkanol compounds used as intermediates are also readily prepared according to well-known literature procedures. Thus, for example, 2-methylaminoethanol is synthesized by heating in a sealed pressure reaction vessel a mixture of methylamine, ethylene oxide, in methanol as solvent, at an elevated temperature of about 140° C. for a time sufficient to bring about substantial completion of the reaction, suitably about 12 hours. The product is isolated by distilling the reaction product mixture. The product, 2-methylaminoethanol, is identified by elemental analyses.

Another alkylaminoalkanol intermediate, 3-(ethylamino)-1-butanol, is prepared according to the following procedure. To a solution of freshly distilled methyl crotonate in methanol there is added ethylamine, with agitation of the mixture. After the initial small rise in temperature of the reaction mixture, it is refluxed for about an hour and distilled. The product, having a boiling point of about 45° C./0.1 mm., is identified by elemental analyses and NMR spectrum, as methyl 3-(ethylamino)butyrate. This ester is then reduced with lithium aluminum hydride in ether solution to yield 3-(ethylamino)-1-butanol, having a boiling point of about 80°-82° C./5 mm., and identified by elemental analyses.

Following, in general, the procedures described hereinbefore, intermediates not available commercially are synthesized. The syntheses of these intermediates are set forth hereinbelow in the Preparations.

PREPARATION 1

5-Chloro-2-hydroxybiphenyl

This material was obtained by fractional distillation, using a spinning band distillation column, of a mixture of chlorophenylphenol isomers identified commercially as Dowicide 32. Material having a boiling point of about 80°-83° C/0.015 mm. was identified as 5-chloro-2-hydroxybiphenyl and was used in the preparation of some of the compounds coming within the scope of the generic formula, above.

PREPARATION 2

3-Chloro-2-hydroxybiphenyl

This compound was separated at the same time as the 5-chloro-2-hydroxybiphenyl (above), by distillation using a spinning band column. This isomer had a boiling point of about 74°-77° C./0.02 mm.

PREPARATION 3

2-Chloro-5-hydroxybiphenyl

This intermediate was prepared stepwise.

The first step was carried out according to the procedure of A. S. Hay, J. Org. Chem. 30, 3577 (1965). Following that procedure, a mixture of 300 g (1.77 moles) of 2-hydroxybiphenyl, 300 g. (2.24 moles) of anhydrous aluminum chloride, and 500 ml. of chlorobenzene was stirred for about 1.5 hours, while being heated on a steam bath. At the end of that time, the reaction mixture was poured over a mixture of ice and dilute aqueous hydrochloric acid. The resulting mixture was extracted several times with ether, and the combined extracts were then washed 2 times with 300 ml. of aqueous 6N hydrochloric acid. The phenol product was extracted from the organic layer with 3 times 500 ml. of 20 percent aqueous sodium hydroxide. These basic extracts were combined, acidified with concentrated aqueous hydrochloric acid, and the acidified mixture extracted several times with ether. The combined ether extracts were washed with water and dried over anhydrous magnesium sulfate. The drying agent was filtered off, the ether evaporated, and the residue distilled through an 8-inch Vigreux column to yield 123 g. of product having a boiling point of about 155°-170° C./10 mm., and a melting point, upon standing of about 62°-68° C. This material was fractionally recrystallized from Skellysolve B (petroleum ether having a boiling point of about 60°-71° C.). A portion of the material was insoluble in the hot petroleum ether. This insoluble material had a melting point of about 155°-158° C., and was recrystallized twice from benzene to yield leaflets having a melting point of about 165° C., and identified as 4-hydroxybiphenyl. The filtrate from these recrystallizations was allowed to cool to room temperature and there was obtained about 65 g. of colorless leaflets having a melting point of about 72°-74° C., and identified as the desired 3-hydroxybiphenyl. The 3-hydroxybiphenyl was used in the next step of the preparation.

A mixture of 40 g. (0.235 mole) of 3-hydroxybiphenyl, 47.7 g. (0.353 mole) of sulfuryl chloride, and 100 ml. of benzene was refluxed for about 3 hours and allowed to stand overnight at room temperature. The reaction product mixture was cooled and extracted with aqueous 6N sodium hydroxide. The basic extracts were acidified and the acidic mixture extracted several times with ether. The combined ether extracts were dried over anhydrous magnesium sulfate. The drying agent was filtered off and the ether was evaporated, leaving an oily residue. The residue was distilled, giving product having a boiling point of about 116°-123° C./0.07 mm. The product was identified as 2-chloro-5-hydroxybiphenyl.

PREPARATION 4

5-(3-Bromopropyloxy)-2-chlorobiphenyl

A mixture of 42 g. of 2-chloro-5-hydroxybiphenyl (from Preparation 3), 100 g. of 1,3-dibromopropane, 13.6 g. of potassium hydroxide, and 200 ml. of methanol was refluxed for about 4 hours. The potassium bromide which had separated was filtered off and the filtrate was evaporated in vacuo to leave a residue. The residue was taken up in about 500 ml. of ether and the ether solution was washed three times with 100 ml. portions of 10 percent aqueous sodium hydroxide, then with water, and was dried over anhydrous sodium sulfate. The drying agent was filtered off and the ether was removed in vacuo, leaving a residue. The residue was distilled two times at reduced pressure to yield product having a boiling point of about 178°-184° C./0.1 mm. The product was identified by elemental analyses as 5-(3-bromopropyloxy)-2-chlorobiphenyl.

Following the same general procedure as described in Preparation 4, the following additional intermediate compounds were prepared and identified. The compounds, together with the principal starting materials used in the preparations, are listed in Preparations 5 through 17 set forth hereinafter.

PREPARATION 5

4-(3-Bromopropyloxy)-3-chlorobiphenyl, having a boiling point of about 167°-170° C./0.1 mm., from 40.9 g. of 3-chloro-4-hydroxybiphenyl and 121.2 g. of 1,3-dibromopropane.

Analyses calculated for $C_{15}H_{14}BrClO$:

|    | Theoretical | Found  |
|----|-------------|--------|
| C  | 55.30%      | 55.62% |
| H  | 4.33        | 4.58   |
| Cl | 10.89       | 10.63  |

-continued

| | Theoretical | Found |
|---|---|---|
| Br | 24.55 | 24.68 |

PREPARATION 6

4-(4-Bromobutyloxy)-3-chlorobiphenyl, identified by its NMR spectrum. Prepared from 3-chloro-4-hydroxybiphenyl and 1,4-dibromobutane.

PREPARATION 7

2-(3-Bromopropyloxy)-5-chlorobiphenyl, having a boiling point of about 130°–135° C./0.15 mm., from 32.6 g. of 5-chloro-2-hydroxybiphenyl and 38.8 g. of 1,3-dibromopropane. Identified by NMR spectrum.

PREPARATION 8

2-(5-Bromopentyloxy)-5-chlorobiphenyl, having a boiling point of about 160°–165° C./0.02 mm., from 25 g. of 5-chloro-2-hydroxybiphenyl and 85 g. of 1,5-dibromopentane.

Analyses calculated for $C_{17}H_{18}BrClO$:

| | Theoretical | Found |
|---|---|---|
| C | 57.70% | 58.47% |
| H | 5.12 | 5.54 |
| Cl | 10.03 | 9.63 |
| Br | 22.61 | 22.30 |

PREPARATION 9

2-(6-Bromohexyloxy)-5-chlorobiphenyl, having a boiling point of about 175°–180° C./0.2 mm., from 23.8 g. of 5-chloro-2-hydroxybiphenyl and 100 g. of 1,6-dibromohexane.

Analyses calculated for $C_{18}H_{20}BrClO$:

| | Theoretical | Found |
|---|---|---|
| C | 58.77% | 60.72% |
| H | 5.48 | 6.75 |
| Cl | 9.65 | 9.43 |
| Br | 21.74 | 20.14 |

PREPARATION 10

2-(2-Bromoethoxy)-5-chlorocyclohexylbenzene, having a boiling point of about 135°–140° C./0.02 mm., from 50 g. of 4-chloro-2-cyclohexylphenol and 150 g. of 1,2-dibromoethane.

PREPARATION 11

2-(3-Bromopropyloxy)-5-chlorocyclohexylbenzene, having a boiling point of about 139°–143° C./0.02 mm., from 50 g. of 4-chloro-2-cyclohexylphenol and 161 g. of 1,3-dibromopropane.

PREPARATION 12

2-(4-Bromobutyloxy)-5-chlorocyclohexylbenzene, having a boiling point of about 146°–149° C./0.02 mm., from 50 g. of 4-chloro-2-cyclohexylphenol and 172 g. of 1,4-dibromopropane.

PREPARATION 13

2-(10-Bromodecyloxy)-5-chlorobiphenyl, having a boiling point of about 230°–235° C./0.1 mm., from 40.8 g. of 5-chloro-2-hydroxybiphenyl and 141 g. of 1,10-dibromodecane.

Analyses calculated for $C_{22}H_{26}BrClO$:

| | Theoretical | Found |
|---|---|---|
| C | 62.34% | 62.50% |
| H | 6.66 | 6.88 |

PREPARATION 14

2-(3-Bromopropylthio)-5-chlorobiphenyl, having a boiling point of about 190°–210° C./1 mm., from 22 g. of 5-chloro-2-mercaptobiphenyl and 111 g. of 1,3-dibromopropane.

PREPARATION 15

2-(3-Chloropropyloxy)-5-chlorobiphenyl, from 204 g. of 5-chloro-2-hydroxybiphenyl and 315 g. of 1,3-dibromopropane. Used crude, without distillation.

PREPARATION 16

2-(4-Bromobutyloxy)-5-chlorobiphenyl, having a boiling point of about 205°–210° C./0.25 mm., from 48.1 g. of 5-chloro-2-hydroxybiphenyl and 127.5 g. of 1,4-dibromobutane. Yield 44.4 g. Identified by NMR spectrum.

PREPARATION 17

2-(2-Bromoethoxy)-5-chlorobiphenyl, from 102 g. of 5-chloro-2-hydroxybiphenyl and 112.8 g. of 1,2-dibromoethane. Used crude, without distillation.

PREPARATION 18

2-Methylaminoethanol

A mixture of 141 g. of methylamine, 100 g. of ethylene oxide and 100 ml. of methanol was heated at about 140° C. for about 12 hours in a pressure vessel. The reaction product mixture was worked up by distilling off the methanol and starting amine and then distilling the residue at reduced pressure to obtain product. The product had a refractive index $\eta_D^{25} = 1.4385$, and was identified by elemental analyses as 2-methylaminoethanol.

Analyses calculated for $C_3H_9NO$:

| | Theoretical | Found |
|---|---|---|
| C | 47.97% | 47.96% |
| H | 12.08 | 11.89 |

PREPARATION 19

3-(Ethylamino)-1-butanol

This intermediate was prepared by a two-step process.

In the first step, to a mixture of 200 g. of freshly distilled methyl crotonate and 250 ml. of methanol, there was added over a period of about 5 minutes, 100 g. of ethylamine, with shaking. After the addition was complete, the temperature of the mixture was about 40° C. During the next half hour, the temperature gradually rose to about 55° C., and then began to drop. The mixture was then refluxed for about 1 hour, and distilled. There was obtained about 245 g. of colorless liquid having a boiling point of about 45° C./0.1 mm. The product was identified by elemental analyses and NMR spectrum as methyl 3-(ethylamino)butyrate.

Analyses calculated for $C_7H_{15}NO_2$:

|   | Theoretical | Found |
|---|---|---|
| C | 57.90% | 58.11% |
| H | 10.41 | 10.53 |
| N | 9.65 | 9.83 |

The ester prepared above, 121 g., was dissolved in anhydrous ether and added dropwise to a suspension of 34.3 g. of lithium aluminum hydride in anhydrous ether. The reaction mixture was stirred overnight at room temperature and then worked up. The product was distilled and found to have a boiling point of about 80°–82° C./5 mm. It was identified by elemental analyses as 3-(ethylamino)-1-butanol.

Analyses calculated for $C_6H_{15}NO$:

|   | Theoretical | Found |
|---|---|---|
| C | 61.49% | 61.13% |
| H | 12.90 | 13.07 |
| N | 11.96 | 11.76 |

PREPARATION 20

1-Chloro-N,N-diethyl-3-butylamine hydrochloride

This intermediate was also prepared stepwise.

To a solution of 245 g. of methyl 3-(ethylamino)butyrate (prepared as described in Step 1 of the preceding Preparation 19) in 500 ml. of ether, was added dropwise 175 g. of acetic anhydride over a period of about 1 hour with continuous stirring. The reaction mixture was then stirred at ambient room temperature for an additional two hours. The reaction mixture was worked up by washing it with dilute aqueous sodium bicarbonate solution and then with water, and the washings discarded. The organic layer was dried over anhydrous sodium sulfate. The drying agent was filtered off and the ether solvent removed in vacuo. The residue which remained was distilled to yield 128 g. of a colorless oil having a boiling point of about 128°–130° C./10 mm. This product was identified by elemental analyses and NMR spectrum as methyl 3-(N-ethylacetamido)butyrate.

Analyses calculated for $C_9H_{17}NO_3$:

|   | Theoretical | Found |
|---|---|---|
| C | 57.73% | 57.45% |
| H | 9.15 | 9.41 |
| N | 7.48 | 7.29 |

The ester prepared above, 128 g., in 500 ml. of anhydrous ether, was added to a mixture of 83.6 g. of lithium aluminum hydride in 2000 ml. of ether, over a period of about 2 hours. The reaction mixture was allowed to stir at ambient room temperature over the weekend. The excess lithium aluminum hydride was destroyed by the successive addition of 88 ml. of water, 66 ml. of aqueous 20 percent sodium hydroxide, and 308 ml. of water. The mixture was then stirred overnight and filtered. The residue on the filter was washed with 1 liter of ether. The aqueous layer of the filtrate was separated and discarded. The ether layer was evaporated by distillation to leave a residue. The residue was distilled under reduced pressure to yield 84 g. of colorless oil having a boiling point of about 73°–75° C./10 mm. The oil was identified by elemental analyses, NMR and IR spectra, as 3-diethylamino-1-butanol.

Analyses calculated for $C_8H_{19}NO$:

|   | Theoretical | Found |
|---|---|---|
| C | 66.15% | 66.13% |
| H | 13.19 | 13.39 |
| N | 9.64 | 9.94 |

This product was used in the next step of the preparation.

A solution of 9 g. of 3-diethylamino-1-butanol was prepared in chloroform and chilled in an ice bath. The solution was saturated with dry hydrogen chloride and then 8.5 g. of thionyl chloride was added dropwise. The reaction product mixture was allowed to warm to room temperature overnight. It was then heated and refluxed until gas evolution ceased. The reaction product mixture was stripped to dryness, the residue dissolved in ethanol and the solution reconcentrated to dryness. This procedure was repeated three times. The residue remaining after the last concentration was identified by elemental analyses as 1-chloro-N,N-diethyl-3-butylamine hydrochloride monohydrate.

Analyses calculated for $C_8H_{18}ClN.HCl.H_2O$:

|   | Theoretical | Found |
|---|---|---|
| C | 44.00% | 44.31% |
| H | 9.64 | 10.14 |
| Cl | 32.60 | 32.56 |

PREPARATION 21

5-Chloro-2-mercaptobiphenyl

This intermediate was prepared in a stepwise manner.

To a mixture of 400 g. of 2-aminobiphenyl and 500 ml. of glacial acetic acid, there was added, in one portion, 400 ml. of acetic anhydride. The resulting exothermic reaction was moderated with cooling. After about 1.5 hours, the reaction mixture was poured into two volumes of water and the crystalline precipitate was filtered off. This crystalline material was recrystallized from three liters of a 1:1 ethanol:water solvent to yield 450 g. of needles having a melting point of about 116°–118° C., and identified as 2-acetamidobiphenyl.

A solution of 800 g. of sodium bicarbonate in 6 l. of water was prepared, and this sodium bicarbonate solution and 450 g. of 2-acetamidobiphenyl were equally divided among three 4-l. beakers, each equipped with a mechanical stirrer. Hypochlorite solution, 2275 ml. of a 5.25 percent aqueous solution of sodium hypochloride (Clorox), was added with stirring during about 30 minutes to each one of the 4-liter beakers. The three reaction mixtures were then allowed to stand overnight. The product which precipitated was collected by filtering the mixtures and was washed with water and air dried. There was thus obtained 470 g. of colorless solid having a melting point of about 68°–70° C., and identified as 2-(N-chloroacetamido)biphenyl.

To a mixture of 2 liters of ethanol and 500 ml. of glacial acetic acid, there was added 470 g. of 2-(N-chloroacetamido)biphenyl. The mixture was cooled to about 5° C., with stirring, and there was added to the mixture in one portion, 2.5 ml. of concentrated aqueous hydrochloric acid. The temperature of the mixture rose during about 5 minutes to about 40° C., and was moderated by cooling with an ice bath. The temperature subsided in about 20 minutes and a negative starch iodide test was obtained. There was then added 26 g. of N-chlorosuccinimide, and the mixture was heated at about 40° C., until no reaction to starch iodide paper was obtained. The reaction mixture was poured into about 8 liters of water. The orange solid which separated was filtered off and sucked as dry as possible on the funnel. The moist solid was dissolved in a mixture of about 1.5 liters of ethanol and 0.5 liter of concentrated aqueous hydrochloric acid. The mixture thus obtained was refluxed overnight. Most of the ethanol was then removed in vacuo, and the remaining mixture was made basic with aqueous 20 percent sodium hydroxide solution. The alkaline mixture was extracted three times with one liter portions of ether. The combined ether extracts were washed with 2 liters of water, dried over anhydrous magnesium sulfate, and the drying agent filtered off. The ether filtrate was concentrated to leave a residual dark oil which weighed about 360 g. This dark oil was distilled. The fractions having a boiling point of about 130°-142° C./0.03 mm. were collected. These fractions crystallized on standing. This product was identified by elemental analyses as 5-chloro-2-aminobiphenyl.

Analyses calculated for $C_{12}H_{10}ClN$:

|   | Theoretical | Found |
|---|---|---|
| C | 70.76% | 71.97% |
| H | 4.95 | 5.45 |

The product consisted of about 95% of the desired compound mixed with about 5% of unchlorinated starting material. The product was used as is for conversion to the thiol in the next step.

The 5-chloro-2-aminobiphenyl used in this reaction was ground to a powder. To a mixture of 300 ml. of concentrated aqueous hydrochloric acid and 300 ml. of ice contained in a three-liter beaker, there was added 256 g. of the powdered 5-chloro-2-aminobiphenyl. The mixture was cooled to a temperature of about 0° C. to −10° C., and there was added dropwise to the mixture a solution of 89.5 g. of sodium nitrite in 180 ml. of water. The mixture thus obtained was added to a solution of 226 g. of potassium xanthate in 300 ml. of water at a temperature of about 45° C., and this mixture was then stirred overnight at a temperature of about 45°-50° C. The reaction mixture was then cooled and poured over about 500 ml. of ice. The organic layer was separated and the aqueous layer extracted several times with ether. The ether extracts and the original organic layer were combined and washed two times with aqueous 10 percent sodium hydroxide solution and then with water to a neutral pH. The ether layer was dried over anhydrous magnesium sulfate, the drying agent filtered off, and the ether filtrate concentrated in vacuo to leave a residue. The residue was dissolved in about 670 ml. of commercial absolute ethanol and was heated to refluxing. To this refluxing solution, there was added 240 g. of potassium hydroxide, and the reaction mixture was refluxed for an additional 7 hours. The reaction mixture was diluted with water and ice and extracted with 1 liter of ether. The aqueous layer was reserved and labeled (A), and the ether extract was discarded. The original basic aqueous layer (A) was made acidic with concentrated aqueous hydrochloric acid and the organic layer which separated was dissolved in ether. This ether solution was washed to a neutral pH with water, dried, and concentrated to leave a residue. This residue was then distilled. The fraction having a boiling point of about 118°-120° C./0.08 mm. weighed 133 g. This material was redistilled on a spinning band column and material having a boiling point of about 92° C./0.06 −0.1 mm., and weighing a total of 90.4 g. was collected and identified by NMR and IR spectra and elemental analyses as 5-chloro-2-mercaptobiphenyl.

Analyses calculated for $C_{12}H_9ClS$:

|   | Theoretical | Found |
|---|---|---|
| C | 65.29% | 65.94% |
| H | 4.11 | 4.25 |
| S | 14.53 | 13.16 |
| Cl | 16.06 | 15.95 |

PREPARATION 22

2-Benzyl-4-chlorophenol

To a solution of sodium ethoxide prepared from 23.0 g. of sodium and one liter of absolute ethanol, there was added 128.5 g. of 4-chlorophenol. Ethanol was distilled off until the distillation temperature reached about 77° C., and the ethanol was replaced by toluene. The distillation was continued until about 500 ml. of distillate had been collected at about 110° C. There was then added dropwise, with stirring, 126.5 g. of benzyl chloride. The reaction mixture turned green and then a dark orange. The reaction product mixture was cooled and acidified and extracted with ethyl ether. The ether extract was extracted with aqueous base to separate the phenol product. The basic solution of the phenol product was then acidified and extracted with ether. The combined ether extracts were dried over anhydrous magnesium sulfate, filtered and distilled in vacuo. The crude product thus obtained was identified as 2-benzyl-4-chlorophenol, and was used without further purification.

Compounds useful in the instant novel method, but not previously disclosed by Lacefield et al., supra, were synthesized following the procedures disclosed therein, using the intermediates prepared as disclosed above, as well as intermediates commercially available. These syntheses are described in the preparations which follow.

PREPARATION 23

1-[3-(5-Chloro-2-biphenylyloxy)propyl]-2-methylpiperidine hydrochloride

A mixture of 20.4 g. (0.10 mole) of 5-chloro-2-hydroxybiphenyl and sodium ethoxide (from 2.3 g. sodium in 150 ml. of absolute ethanol) was prepared, and there was added thereto 21 g. (0.12 mole) of 1-(3-chloropropyl)-2-methylpiperidine. The reaction mixture was refluxed overnight, allowed to cool, and was filtered to remove the precipitated sodium chloride. The filtrate was concentrated in vacuo to leave a residue. The residue was taken up in ether and the ether solution was extracted several times with aqueous 10 percent hydrochloric acid. The combined aqueous acid extracts were cooled, made basic with aqueous sodium hydroxide solution, and the basic mixture extracted with ether. The combined ether extracts were dried over anhydrous sodium sulfate. The drying agent was filtered off and the dry ether filtrate cooled in an ice bath and saturated with anhydrous hydrogen chloride. The precipitate which formed was filtered off and recrystallized from a mixture of ethanol and ether. There was obtained product having a melting point of about 170°–171° C., which product was identified by pK$_a$ and elemental analyses as 1-[3-(5-chloro-2-biphenylyloxy)-propyl]-2-methylpiperidine hydrochloride.

Analyses calculated for $C_{21}H_{26}ClNO·HCl$:

|   | Theoretical | Found |
|---|---|---|
| C | 66.30% | 66.01% |
| H | 7.16 | 7.33 |

Following the general procedure of Preparation 23, additional compounds were prepared and identified either as the free base or as an acid addition salt thereof.

PREPARATION 24

3-(5-Chloro-2-biphenylyloxy)-N,N,1-trimethylpropylamine, as an oil, from 102 g. of 5-chloro-2-hydroxybiphenyl and 102 g. of 3-chloro-N,N,1-trimethylpropylamine. Identified by elemental analyses.

Analyses calculated for $C_{18}H_{22}ClNO$:

|   | Theoretical | Found |
|---|---|---|
| C | 71.15% | 70.94% |
| H | 7.30 | 7.55 |

PREPARATION 25

3-(5-Chloro-2-biphenylyloxy)-N,N,1-trimethylpropylamine hydrobromide, having a melting point of about 131°–133° C., from 6 g. of the free base (Preparation 24) in ether plus hydrogen bromide.

Analyses calculated for $C_{18}H_{22}ClNO·HBr$:

|   | Theoretical | Found |
|---|---|---|
| C | 56.18% | 56.32% |
| H | 6.02 | 6.10 |

PREPARATION 26

3-(2-Biphenylylthio)-N,N,1-trimethylpropylamine hydrochloride, having a melting point of about 127°–129° C., from 7.4 g. of 2-mercaptobiphenyl and 8.2 g. of 3-chloro-N,N,1-trimethylpropylamine.

Analyses calculated for $C_{18}H_{23}NS·HCl$:

|   | Theoretical | Found |
|---|---|---|
| C | 67.16% | 67.31% |
| H | 7.52 | 7.50 |

PREPARATION 27

3-(4-Biphenylyloxy)-N,N,1-trimethylpropylamine hydrochloride, having a melting point of about 160°–163° C., from 8.5 g. of 4-hydroxybiphenyl and 10.3 g. of 3-chloro-N,N,1-trimethylpropylamine.

Analyses calculated for $C_{18}H_{23}NO·HCl$:

|   | Theoretical | Found |
|---|---|---|
| C | 70.68% | 70.51% |
| H | 7.91 | 8.17 |

PREPARATION 28

3-(2-Benzyl-4-chlorophenoxy)-N,N-dimethylpropylamine hydrochloride, having a melting point of about 140°–141° C., from 21.8 g. of 2-benzyl-4-chlorophenol and 12.2 g. of dimethylaminopropyl chloride. Identified by elemental analyses.

Analyses calculated for $C_{18}H_{22}ClNO·HCl$:

|   | Theoretical | Found |
|---|---|---|
| C | 63.53% | 63.47% |
| H | 6.81 | 6.90 |
| N | 4.12 | 3.86 |

PREPARATION 29

3-(5-Chloro-2-biphenylyloxy)-N-ethyl-1-methylpropylamine hydrochloride

The potassium salt of 20.4 g. (0.10 mole) of 5-chloro-2-hydroxybiphenyl was prepared in methanol and the mixture concentrated in vacuo to dryness. The solid residue was suspended in benzene and 20 g. (0.10 mole) of 4-chloro-N-ethyl-N-formyl-2-butylamine was added thereto dropwise. The reaction mixture was refluxed overnight. The reaction product mixture was worked up by adding water and ether, and the ether-organic layer was separated and washed with water. The organic layer was dried over anhydrous sodium sulfate, the drying agent filtered off, and the filtrate concentrated to dryness. This residue was taken up in aqueous 6N hydrochloric acid and refluxed for three days. The reaction mixture was cooled and made basic with aqueous sodium hydroxide solution. The basic aqueous solution was extracted with ether, and the ether extracts discarded.

The basic aqueous layer, from above, was refluxed overnight with added 20 percent aqueous alkali. The reaction mixture was cooled and extracted with ether. The combined ether extracts were dried over anhydrous sodium sulfate. The drying agent was filtered off and the dry ether solution was saturated with anhydrous hydrogen chloride. A precipitate formed, which was filtered off and recrystallized to yield product having a melting point of about 158°–159° C. The product was identified by elemental analyses as 3-(5-chloro-2-biphenylyloxy)-N-ethyl-1-methylpropylamine hydrochloride.

Analyses calculated for $C_{18}H_{22}ClNO·HCl$:

|   | Theoretical | Found |
|---|---|---|
| C | 63.53% | 63.35% |
| H | 6.81 | 6.57 |

Following the general procedure of Preparation 29, the following additional compounds were prepared and identified. The principal starting materials, and the weights thereof, used in the preparations are also listed.

PREPARATION 30

3-(5-Chloro-2-biphenylyloxy)-N,N-diethyl-1-methylpropylamine, having a boiling point of about 155°–160° C./0.02 mm., from 12 g. of 3-chloro-N,N-diethyl-1-methylpropylamine hydrochloride and 10.2 g. of 5-chloro-2-hydroxybiphenyl.

Analyses calculated for $C_{20}H_{26}ClNO$:

|   | Theoretical | Found |
|---|---|---|
| C | 72.57% | 72.09% |
| H | 7.89 | 8.79 |
| N | 4.22 | 4.52 |

PREPARATION 31

3-(5-Bromo-2-biphenylyloxy)-N,N,1-trimethylpropylamine hydrochloride, having a melting point of about 163°–164° C., from 10.0 g. of 3-chloro-N,N,1-trimethylpropylamine and 12.5 g. of 5-bromo-2-hydroxybiphenyl.

Analyses calculated for $C_{18}H_{22}BrNO·HCl$:

|   | Theoretical | Found |
|---|---|---|
| C | 56.18% | 55.91% |
| H | 6.03 | 6.01 |

PREPARATION 32

3-(2-Biphenylyloxy)-N,N,1-trimethylpropylamine hydrochloride, having a melting point of about 142°–143° C., and weighing 4.2 g., from 10 g. of 2-hydroxybiphenyl and 24.5 g. of 3-chloro-N,N,1-trimethylpropylamine. Identified by NMR spectrum and elemental analyses.

Analyses calculated for $C_{18}H_{22}NO·HCl$:

|   | Theoretical | Found |
|---|---|---|
| C | 70.68% | 69.83% |
| H | 7.91 | 8.06 |
| N | 4.58 | 4.55 |

PREPARATION 33

3-(5-Chloro-2-biphenylyloxy)-N,N,2-trimethylpropylamine hydrobromide

In an autoclave equipped with a glass liner, a mixture was prepared of 30 g. (0.1 mole) of 2-(3-chloro-2-methylpropoxy)-5-chlorobiphenyl, 100 g. (2.2 moles) of anhydrous dimethylamine, and 75 ml. of commercial absolute ethanol. The autoclave was then sealed and heated to a temperature of about 120° C. for about 8 hours. The autoclave was cooled and opened, and the reaction product mixture removed. The mixture was distilled to remove solvent and excess dimethylamine, and the residue which remained was dissolved in about 500 ml. of dilute aqueous hydrochloric acid. The acidic aqueous solution was washed with ether, made alkaline with aqueous 50 percent sodium hydroxide solution and extracted with ether. The ether extracts were combined and washed with several portions of water. The ether extracts were dried over anhydrous sodium sulfate, the drying agent filtered off, and the solvent removed in vacuo, leaving a residue. The residue was distilled at reduced pressure to yield material having a boiling point of about 155°–165° C./0.05 mm. This material was used to prepare the hydrobromide acid addition salt, which salt had a melting point of about 106°–109° C. It was identified by elemental analyses as 3-(5-chloro-2-biphenylyloxy)-N,N,2-trimethylpropylamine hydrobromide.

Analyses calculated for $C_{18}H_{22}ClNO·HBr$:

|   | Theoretical | Found |
|---|---|---|
| C | 56.18% | 57.29% |
| H | 5.98 | 6.27 |

Following the same general procedure of Preparation 33, additional compounds were prepared and identified. The quantities of the principal starting materials used in the preparation of the compounds are also included.

PREPARATION 34

4-(2-Biphenylyloxy)-N,N-dimethylbutylamine hydrochloride, having a melting point of about 96°–99° C., from 21 g. of 4-(2-biphenylyloxy)butyl bromide and 100 g. of dimethylamine.

Analyses calculated for $C_{18}H_{23}NO·HCl$:

|   | Theoretical | Found |
|---|---|---|
| C | 70.67% | 68.60% |
| H | 7.90 | 8.16 |

PREPARATION 35

4-[3-(5-Chloro-2-biphenylyloxy)propyl]morpholine hydrochloride, having a melting point of about 199°–200° C., from 15 g. of 2-(3-bromopropyloxy)-5-chlorobiphenyl and 100 g. of morpholine.

Analyses calculated for $C_{19}H_{22}ClNO_2·HCl$:

|   | Theoretical | Found |
|---|---|---|
| C | 61.97% | 61.89% |
| H | 6.29 | 6.43 |

PREPARATION 36

N-Allyl-3-(5-chloro-2-biphenylyloxy)propylamine hydrochloride, having a melting point of about 165° C. (dec.), from 15 g. of 2-(3-chloropropyloxy)-5-chlorobiphenyl and 100 g. of allylamine.

Analyses calculated for $C_{18}H_{20}ClNO·HCl$:

|   | Theoretical | Found |
|---|---|---|
| C | 63.91% | 64.04% |
| H | 6.26 | 6.46 |

PREPARATION 37

N-(t-Butyl)-6-(5-chloro-2-biphenylyloxy)hexylamine hydrochloride, having a melting point of about 132°–135° C., and weighing 3.1 g., from 8 g. of 2-(6-bromohexyloxy)-5-chlorobiphenyl and 40 ml. of t-butylamine. Identified by NMR spectrum and elemental analyses.

Analyses calculated for $C_{22}H_{29}ClNO·HCl$:

|   | Theoretical | Found |
|---|---|---|
| C | 66.81% | 66.41% |
| H | 7.64 | 7.63 |
| N | 3.54 | 3.80 |

PREPARATION 38

3-(2-Chloro-4-biphenylyloxy)-N-cyclohexylpropylamine hydrochloride, having a melting point of about 202°–203° C., and weighing 4.2 g., from 5 g. of 4-(3-bromopropyloxy)-2-chlorobiphenyl and 25 ml. of cyclohexylamine. Identified by NMR spectrum and elemental analyses.

Analyses calculated for $C_{21}H_{26}ClNO.HCl$:

|   | Theoretical | Found |
|---|---|---|
| C | 66.29% | 66.25% |
| H | 7.15 | 7.17 |
| N | 3.68 | 3.53 |

PREPARATION 39

N-(t-Butyl)-3-(5-chloro-2-biphenylyloxy)propylamine hydrochloride, having a melting point of about 187°–189° C., from 15 g. of 2-(3-chloropropyloxy)-5-chlorobiphenyl and 100 g. of t-butylamine.

Analyses calculated for $C_{19}H_{24}ClNO.HCl$:

|   | Theoretical | Found |
|---|---|---|
| C | 64.40% | 64.46% |
| H | 7.11 | 7.30 |

PREPARATION 40

N-Butyl-3-(5-chloro-2-biphenylyloxy)propylamine hydrochloride, having a melting point of about 136°–138° C., from 15 g. of 2-(3-chloropropyloxy)-5-chlorobiphenyl and 100 g. of n-butylamine.

Analyses calculated for $C_{19}H_{24}ClNO.HCl$:

|   | Theoretical | Found |
|---|---|---|
| C | 64.40% | 64.43% |
| H | 7.11 | 7.44 |

PREPARATION 41

3-(5-Chloro-2-biphenylyloxy)-N-isopropylpropylamine hydrochloride, having a melting point of about 141°–143° C., from 15 g. of 2-(3-chloropropyloxy)-5-chlorobiphenyl and 100 g. of isopropylamine.

Analyses calculated for $C_{18}H_{22}ClNO.NCl$:

|   | Theoretical | Found |
|---|---|---|
| C | 63.53% | 63.87% |
| H | 8.81 | 7.12 |

PREPARATION 42

4-(5-Chloro-2-biphenylyloxy)-di-n-butylamine hydrochloride, having a melting point of about 160°–161° C., from 15 g. of 2-(4-bromobutyloxy)-5-chlorobiphenyl and excess n-butylamine.

Analyses calculated for $C_{20}H_{26}ClNO.HCl$:

|   | Theoretical | Found |
|---|---|---|
| C | 65.21% | 65.03% |
| H | 7.39 | 7.76 |

PREPARATION 43

N-[4-(5-Chloro-2-biphenylyloxy)butyl]cyclohexylamine hydrochloride, having a melting point of about 196°–197° C., from 15 g. of 2-(4-bromobutyloxy)-5-chlorobiphenyl and excess cyclohexylamine.

|   | Theoretical | Found |
|---|---|---|
| C | 66.99% | 67.03% |
| H | 7.41 | 7.50 |

PREPARATION 44

4-(5-Chloro-2-biphenylyloxy)-N,N-diisopropylbutylamine hydrochloride, having a melting point of about 189°–191° C. from 15 g. of 2-(4-bromobutyloxy)-5-chlorobiphenyl and excess diisopropylamine.

Analyses calculated for $C_{22}H_{30}ClNO.HCl$:

|   | Theoretical | Found |
|---|---|---|
| C | 66.99% | 66.71% |
| H | 7.41 | 8.17 |

PREPARATION 45

3-(2-Chloro-5-biphenylyloxy)-N,N-diethylpropylamine hydrochloride, having a melting point of about 174°–175° C., from 15 g. of 3-(3-brompropyloxy)-6-chlorobiphenyl and excess diethylamine.

Analyses calculated for $C_{19}H_{24}ClNO.HCl$:

|   | Theoretical | Found |
|---|---|---|
| C | 64.40% | 64.73% |
| H | 7.11 | 7.49 |

PREPARATION 46

3-(4-Chloro-o-biphenylylthio)-N-cyclohexylpropylamine hydrochloride, having a melting point of about 270° C., from 15 g. of 2-(3-bromopropylthio)-5-chlorobiphenyl and excess cyclohexylamine.

Analyses calculated for $C_{21}H_{26}ClNS.HCl$:

|   | Theoretical | Found |
|---|---|---|
| C | 63.62% | 64.66% |
| H | 6.87 | 7.37 |

PREPARATION 47

10-(5-Chloro-2-biphenylyloxy)-N-ethyl-N-(2-hydroxyethyl)decylamine hydrochloride, having a melting point of about 65°–67° C., from 6 g. of 2-(10-bromodecyloxy)-5-chlorobiphenyl and an excess of 2-ethylaminoethanol.

Analyses calculated for $C_{26}H_{38}ClNO_2.HCl$:

|   | Theoretical | Found |
|---|---|---|
| C | 66.65% | 66.27% |
| H | 8.39 | 8.43 |

PREPARATION 48

10-(5-Chloro-2-biphenyloxy)-N,N-diethyldecylamine hydrochloride, having a melting point of about 86°–87° C., from 6 g. of 2-(10-bromodecyloxy)-5-chlorobiphenyl and an excess of diethylamine.

Analyses calculated for $C_{26}H_{39}ClNO.HCl$:

|   | Theoretical | Found |
|---|---|---|
| C | 69.00% | 68.87% |
| H | 8.69 | 8.83 |

PREPARATION 49

N-(t-Butyl)-3-(5-chloro-2-biphenylyloxy)-N-(2-hydroxyethyl)propylamine hydrochloride, having a melting point of about 122°–125° C., from 10 g. of 2-(3-bromopropyloxy)-5-chlorobiphenyl and excess 2-(t-butylamino)ethanol.

Analyses calculated for $C_{21}H_{28}ClNO_2\cdot HCl$:

|   | Theoretical | Found |
|---|---|---|
| C | 63.31% | 63.53% |
| H | 7.33 | 7.27 |

PREPARATION 50

3-(5-Chloro-2-biphenylyloxy)-N-(2-hydroxyethyl)-N-neopentylpropylamine hydrochloride, having a melting point of about 124°–127° C., from 10 g. of 2-(3-bromopropyloxy)-5-chlorobiphenyl and excess 2-neopentylaminoethanol.

Analyses calculated for $C_{22}H_{30}ClNO_2\cdot HCl$:

|   | Theoretical | Found |
|---|---|---|
| C | 64.07% | 63.21% |
| H | 7.57 | 8.03 |

PREPARATION 51

N-(n-Butyl)-3-(5-chloro-2-biphenylyloxy)-N-(2-hydroxyethyl)propylamine hydrochloride, having a melting point of about 115°–117° C., from 10 g. of 2-(3-bromopropyloxy)-5-chlorobiphenyl and 10 g. of 2-(n-butylamino)ethanol.

Analyses calculated for $C_{21}H_{28}ClNO_2\cdot HCl$:

|   | Theoretical | Found |
|---|---|---|
| C | 63.31% | 63.32% |
| H | 7.34 | 7.53 |

PREPARATION 52

N-(t-Butyl)-3-(2-chloro-4-biphenylyloxy)propylamine hydrochloride, having a melting point of about 212°–214° C., from 5 g. of 4-(3-bromopropyloxy)-3-chlorobiphenyl and 25 ml. of t-butylamine.

Analyses calculated for $C_{19}H_{24}ClNO\cdot HCl$:

|   | Theoretical | Found |
|---|---|---|
| C | 64.40% | 64.29% |
| H | 7.11 | 6.75 |
| N | 3.95 | 3.85 |

PREPARATION 53

N-(t-Butyl)-5-(5-chloro-2-biphenylyloxy)pentylamine hydrochloride, having a melting point of about 169°–171° C., from 5 g. of 2-(5-bromopentyloxy)-5-chlorobiphenyl and 25 ml. of t-butylamine.

Analyses calculated for $C_{21}H_{28}ClNO\cdot HCl$:

|   | Theoretical | Found |
|---|---|---|
| C | 65.95% | 65.99% |
| H | 7.63 | 7.36 |
| N | 3.66 | 3.43 |
| Cl | 18.56 | 18.86 |

PREPARATION 54

N-Adamantyl-5-(5-chloro-2-biphenylyloxy)pentylamine hydrochloride

A mixture of 5 g. of 2-(5-bromopentyloxy)-5-chlorobiphenyl and 5 g. of 1-aminoadamantane was heated at about 135° C. in an oil bath overnight. The reaction mixture was taken up in ether and aqueous 20 percent sodium hydroxide. The mixture was extracted with ether and the combined ether extracts were then extracted with aqueous 10 percent hydrochloric acid. Crystals separated from the aqueous hydrochloric acid solution, which crystals were filtered off and recrystallized from ethanol. There was obtained 2.5 g. of a colorless solid having a melting point of about 235°–236° C. The solid was identified by elemental analyses and NMR spectrum as N-adamantyl-5-(5-chloro-2-biphenylyloxy)pentylamine hydrochloride.

Analyses calculated for $C_{27}H_{34}ClNO\cdot HCl$:

|   | Theoretical | Found |
|---|---|---|
| C | 70.42% | 70.38% |
| H | 7.66 | 7.73 |
| Cl | 15.40 | 15.17 |

Following the general procedure of Preparation 54, additional compounds were prepared and identified as the free base or the acid addition salt thereof. The compounds, together with the principal starting materials and quantities thereof used in the preparations, are listed in the preparations set forth hereinafter.

PREPARATION 55

3-(5-Chloro-2-biphenylyloxy)-N-cyclohexylpropylamine hydrochloride, having a melting point of about 212°–213° C., from 32.5 g. of 2-(3-bromopropyloxy)-5-chlorobiphenyl and 50 g. of cyclohexylamine.

Analyses calculated for $C_{21}H_{26}ClNO\cdot HCl$:

|   | Theoretical | Found |
|---|---|---|
| C | 66.31% | 66.14% |
| H | 7.16 | 7.34 |

PREPARATION 56

3-(5-Chloro-2-biphenylyloxy)-N-phenylpropylamine hydrochloride, having a melting point of about 130°–131° C., from 25 g. of 2-(3-bromopropyloxy)-5-chlorobiphenyl and 50 ml. of aniline.

Analyses calculated for $C_{21}H_{18}ClNO\cdot HCl$:

|   | Theoretical | Found |
|---|---|---|
| C | 67.75% | 67.92% |
| H | 5.14 | 5.79 |
| N | 3.76 | 3.79 |

PREPARATION 57

3-(5-Chloro-2-biphenylyloxy)-3'-methoxy-di(n-propyl)amine, having a boiling point of about 174°–175° C./0.01 mm., from 25 g. of 2-(3-bromopropyloxy)-5-chlorobiphenyl and 50 ml. of 3-methoxypropylamine.

Analyses calculated for $C_{19}H_{24}ClNO_2$:

|   | Theoretical | Found |
|---|---|---|
| C | 67.60% | 67.86% |
| H | 6.88 | 7.27 |
| N | 4.38 | 4.64 |

PREPARATION 58

N-Benzyl-3-(5-chloro-2-biphenylyloxy)propylamine, having a boiling point of about 193°–195° C./0.01 mm., from 10 g. of 2-(3-bromopropyloxy)-5-chlorobiphenyl and 25 ml. of benzylamine.

Analyses calculated for $C_{22}H_{22}ClNO$:

|   | Theoretical | Found |
|---|---|---|
| C | 75.09% | 75.17% |
| H | 6.30 | 6.58 |
| N | 3.98 | 4.23 |

PREPARATION 59

N-(t-Butyl)-3-(4-chloro-2-biphenylyloxy)propylamine, having a boiling point of about 140°–142° C./0.01 mm., from 10 g. of 2-(3-bromopropyloxy)-5-chlorobiphenyl and 25 ml. of t-butylamine.

Analyses calculated for $C_{19}H_{24}ClNO$:

|   | Theoretical | Found |
|---|---|---|
| C | 71.79% | 71.86% |
| H | 7.61 | 7.72 |
| N | 4.41 | 4.67 |

PREPARATION 60

1-[3-(5-Chloro-2-biphenylyloxy)propyl]pyrrolidine, having a boiling point of about 158°–160° C./0.01 mm., from 10 g. of 2-(3-bromopropyloxy)-5-chlorobiphenyl and 25 ml. of pyrrolidine.

Analyses calculated for $C_{19}H_{22}ClNO$:

|   | Theoretical | Found |
|---|---|---|
| C | 72.25% | 72.53% |
| H | 7.02 | 7.25 |
| N | 4.44 | 4.20 |

PREPARATION 61

N-(n-Butyl)-3-(5-chloro-2-biphenylyloxy)propylamine, having a boiling point of about 148°–150° C./0.05 mm., from 10 g. of 2-(3-bromopropyloxy)-5-chlorobiphenyl and 25 ml. of n-butylamine.

Analyses calculated for $C_{19}H_{24}ClNO$:

|   | Theoretical | Found |
|---|---|---|
| C | 71.79% | 72.03% |
| H | 7.61 | 7.62 |
| N | 4.41 | 4.48 |

PREPARATION 62

3-(5-Chloro-2-biphenylyloxy)-N-(2-hydroxyethyl)-propylamine hydrochloride, having a melting point of about 101°–103° C., from 10 g. of 2-(3-chloropropyloxy)-5-chlorobiphenyl and excess ethanolamine.

Analyses calculated for $C_{17}H_{20}ClNO_2 \cdot HCl$:

|   | Theoretical | Found |
|---|---|---|
| C | 59.65% | 59.59% |
| H | 6.18 | 6.71 |

PREPARATION 63

3-(5-Chloro-2-biphenylyloxy)-N,N-bis(2-hydroxyethyl)propylamine hydrochloride, having a melting point of about 90°–92° C., from 10 g. of 2-(3-chloropropyloxy)-5-chlorobiphenyl and excess diethanolamine.

Analyses calculated for $C_{19}H_{24}ClNO_3 \cdot HCl$:

|   | Theoretical | Found |
|---|---|---|
| C | 59.07% | 59.12% |
| H | 6.52 | 6.77 |

PREPARATION 64

N-Adamantyl-3-(5-chloro-2-biphenylyloxy)propylamine hydrochloride, having a melting point of about 206°–208° C., from 10 g. of 2-(3-chloropropyloxy)-5-chlorobiphenyl and excess 1-aminoadamantane.

Analyses calculated for $C_{25}H_{30}ClNO \cdot HCl$:

|   | Theoretical | Found |
|---|---|---|
| C | 69.44% | 69.37% |
| H | 7.23 | 7.53 |

PREPARATION 65

1-[3-(5-Chloro-2-biphenylyloxy)propyl]-4-(2-hydroxyethyl)piperazine dihydrochloride, having a melting point of about 225°–227° C., from 10 g. of 2-(3-chloropropyloxy)-5-chlorobiphenyl and excess (2-hydroxyethyl)piperazine.

Analyses calculated for $C_{21}H_{27}ClN_2O_2 \cdot 2HCl$:

|   | Theoretical | Found |
|---|---|---|
| C | 56.32% | 55.95% |
| H | 6.53 | 6.93 |

PREPARATION 66

4-[3-(3-Chloro-2-biphenylyloxy)propyl]-1-(2-hydroxyethyl)piperazine dihydrochloride, having a melting point of about 200°–201° C., from 5 g. of 2-(3-chloropropyloxy)-3-chlorobiphenyl and excess (2-hydroxyethyl)piperazine.

Analyses calculated for $C_{21}H_{27}ClN_2O_2 \cdot 2HCl$:

|   | Theoretical | Found |
|---|---|---|
| C | 56.33% | 56.06% |
| H | 6.53 | 6.72 |

PREPARATION 67

N-Adamantyl-3-(5-chloro-2-biphenylylthio)propylamine hydrochloride

A mixture of 15 g. of 2-(3-bromopropylthio)-5-chlorobiphenyl and an excess of 1-aminoadamantane was heated in an oil bath at about 120° C. for about 4 hours. The reaction mixture was worked up and the product was isolated as the hydrochloride acid addition salt in the manner described in previous examples. The product had a melting point of about 304°–305° C., and was identified as N-adamantyl-3-(5-chloro-2-biphenylylthio)propylamine hydrochloride.

Analyses calculated for $C_{25}H_{30}ClNS \cdot HCl$:

|   | Theoretical | Found |
|---|---|---|
| C | 66.95% | 66.70% |
| H | 6.97 | 7.07 |
| Cl | 8.59 | 8.94 |

Following the general procedure of Preparation 67, additional compounds were prepared and identified. The compounds, together with the principal starting materials and weights thereof used in the preparations, are listed in the examples set forth hereinafter.

PREPARATION 68

N-Adamantyl-4-(2-biphenylylthio)butylamine hydrochloride, having a melting point of about 216°–217° C., and weighing 2 g., from 5 g. of 2-(4-bromobutylthio)biphenyl and 5 g. of 1-aminoadamantane. Identified by NMR spectrum and elemental analyses.

Analyses calculated for $C_{26}H_{32}NS \cdot HCl$:

|   | Theoretical | Found |
|---|---|---|
| C | 73.12% | 72.97% |
| H | 7.79 | 8.19 |
| Cl | 8.30 | 8.72 |

PREPARATION 69

3-(2-Biphenylylthio)-N-cyclohexylpropylamine hydrochloride, having a melting point of about 247°–249° C., and weighing 2.5 g., from 5 g. of 2-(3-bromopropylthio)biphenyl and 5 g. of cyclohexylamine. Identified by NMR spectrum and elemental analyses.

Analyses calculated for $C_{21}H_{27}NS \cdot HCl$:

|   | Theoretical | Found |
|---|---|---|
| C | 69.68% | 69.45% |
| H | 7.80 | 7.94 |
| S | 8.86 | 8.88 |
| Cl | 9.80 | 10.00 |

PREPARATION 70

N-Adamantyl-3-(2-biphenylylthio)propylamine hydrochloride, having a melting point of about 255°–257° C., and weighing 2.5 g., from 5 g. of 2-(3-bromopropylthio)biphenyl and 5 g. of 1-aminoadamantane. Identified by NMR spectrum and elemental analyses.

Analyses calculated for $C_{24}H_{31}NS \cdot HCl$:

|   | Theoretical | Found |
|---|---|---|
| C | 72.69% | 72.82% |
| H | 7.57 | 8.24 |
| S | 7.76 | 7.85 |
| Cl | 8.59 | 8.94 |

The novel method of this invention is practiced by adding the chemicals to the water containing the aquatic weeds. The chemicals may be applied as dusts when admixed with a powdered solid carrier such as various mineral silicates, e.g. mica, talc, pyrophyllite, and clays. The chemicals may be mixed with surface-active dispersing agents to form herbicidal concentrates to facilitate dispersion in water and to improve the wetting properties when used as sprays. If desired, the chemicals may be mixed with a powdered solid carrier together with a surface-active dispersing agent so that a wettable powder may be obtained which may be applied directly or which may be shaken up with water to make an aqueous dispersion for application in that form. The chemicals may be dissolved in an oil such as a hydrocarbon or chlorinated hydrocarbon oil, and the oil solution of the chemical dispersed in water with the aid of a surface-active dispersing agent to give a sprayable aqueous dispersion. Such surface-active dispersing agents may be anionic, nonionic, or cationic surface-active agents. Such surface-active agents are well known and reference is made to Hoffmann et al., U.S. Pat. No. 2,614,916, columns 2–4, for detailed examples of the same. The chemicals of the present invention may be applied by the aerosol method. Solutions for the aerosol treatment may be prepared by dissolving the chemical directly in the aerosol carrier, which is a liquid under pressure, but which is a gas at ordinary temperature (e.g. 20° C.) and atmospheric pressure, or the aerosol solution may be prepared by first dissolving the chemical in a less volatile solvent, and then admixing such solution with the highly volatile liquid aerosol carrier.

The invention is practiced by adding to the water a sufficient amount of the chemical that a concentration of from about 0.5 to about 10 parts per million is obtained, preferably sufficient chemical to provide a concentration of from about 0.5 to about 2 parts per million.

The optimum concentration for any specific control problem varies with the temperature, the species to be controlled, and the shape of the water body to be treated. At higher water temperatures, less chemical is generally required for a given degree of control than is needed at lower temperatures.

In considering the treatment of moving streams for the purpose of destroying flora fixed therein, special account must be taken of the fact that the chemicals will pass over the area to be treated and that the concentration during the contact period is dependent upon the water flow rate, the rate of chemical addition, and the period of addition.

The novel herbicidal method and compositions are illustrated by the following experiments conducted in the laboratory.

EXPERIMENT 1

In a first test, the plants used were coontail, *Ceratophyllum demersum* L.; Florida elodea, *Hydrilla verticillata* (L.F.); and duckweed, *Lemna minor* L. The plants were prepared by cutting four-inch terminal sprigs of the coontail and elodea, and selecting approximately enough duckweed to just cover the surface of the water in a 10 ml. beaker (approximately 30 plants). The coontail, elodea and duckweed were then placed in beakers containing 750 ml. of dechlorinated water containing the compounds.

The compounds for this test were formulated in the following manner. Seventeen mg. of compound was weighed into a 12 ml. disposable vial. To the vial containing the compound was added 1 ml. of acetone followed by 10 ml. of aqueous 0.1 percent polyoxyethylene sorbitan monooleate. This stock solution was then pipetted into the beakers at volumes of 0.45 ml. and 4.55 ml., to obtain 1 and 10 ppm. concentration of test compound in 750 ml. of water. Control beakers containing 750 ml. of water together with the solvents used in the formulations were also run. Other concentrations of the test compounds needed for testing were obtained by serial dilution of the 1 and 10 ppm. concentration solutions.

Observations of the effect of the compounds on the plants were made over a seven-day period. The scale for rating the aquatic herbicidal activity of the compounds was on a basis of 1–5, as follows:

1 = no effect
2 = slight effect
3 = moderate effect
4 = heavy effect
5 = complete kill The compounds tested are listed hereinafter.

1. 2-(5-Chloro-2-biphenylyloxy)-N,N-dimethylethylamine hydrobromide
2. 3-(5-Chloro-2-biphenylyloxy)-N,N-dimethylpropylamine hydrochloride
3. 3-(2-Cyclohexylphenoxy)-N,N-dimethyl-propylamine hydrochloride
4. 3-(2-Biphenylyloxy)-N,N-dimethyl-propylamine hydrochloride
5. 3-(2-Benzyl-4-chlorophenoxy)-N,N-dimethyl-propylamine hydrochloride
6. 3-(5-Chloro-2-biphenylyloxy)-N,N,1-trimethylpropylamine hydrobromide
7. 3-(5-Chloro-2-biphenylyloxy)-N-ethyl-1-methylpropylamine hydrochloride
8. 3-(2-Biphenylylthio)-N,N,1-trimethylpropylamine hydrochloride
9. N-(t-Butyl)-3-(5-chloro-2-biphenylyloxy)-N-(2-hydroxyethyl)propylamine hydrochloride
10. 3-(5-Chloro-2-biphenylyloxy)-N-(2-hydroxyethyl)-N-neopentylpropylamine hydrochloride
11. 3-(4-Biphenylyloxy)-N,N,1-trimethylpropylamine hydrochloride
12. 3-(2-Biphenylyloxy)-N,N,1-trimethylpropylamine hydrochloride
13. 3-(5-Chloro-2-biphenylyloxy)-N-cyclohexylpropylamine hydrochloride
14. N-Adamantyl-3-(5-chloro-2-biphenylylthio)-propylamine hydrochloride
15. 3-(5-Chloro-2-biphenylyloxy)-N,N-diethyl-1-methylpropylamine
16. 3-(5-Bromo-2-biphenylyloxy)-N,N,1-trimethylpropylamine hydrochloride
17. 3-(5-Chloro-2-biphenylyloxy)-N-ethylpropylamine hydrochloride
18. 4-[3-(5-Chloro-2-biphenylyloxy)propyl]morpholine hydrochloride
19. 3-(5-Chloro-2-biphenylyloxy)-N,N,2-trimethylpropylamine hydrobromide
20. 3-(5-Chloro-2-biphenylyloxy)-N,N-diethylpropylamine hydrochloride
21. 4-(2-Biphenylyloxy)-N,N-dimethylbutylamine hydrochloride
22. 3-(5-Chloro-2-biphenylyloxy)propylamine
23. N-Allyl-3-(5-chloro-2-biphenylyloxy)propylamine hydrochloride
24. 3-(5-Chloro-2-biphenylyloxy)-N-isopropylpropylamine hydrochloride
25. N-(n-Butyl)-3-(5-chloro-2-biphenylyloxy)-propylamine hydrochloride
26. N-(t-Butyl)-3-(5-chloro-2-biphenylyloxy)-propylamine hydrochloride
27. 1-[3-(5-Chloro-2-biphenylyloxy)propyl]-2-methylpiperidine hydrochloride
28. 3-(4-Chloro-2-biphenylyloxy)-N-(2-hydroxyethyl)propylamine hydrochloride
29. 3-(5-Chloro-2-biphenylyloxy)-N-ethyl-N-(2-hydroxyethyl)propylamine hydrochloride
30. 3-(5-Chloro-2-biphenylyloxy)-N,N-bis(2-hydroxyethyl)propylamine hydrochloride
31. N-Adamantyl-3-(5-chloro-2-biphenylyloxy)-propylamine hydrochloride
32. 1-[3-(5-Chloro-2-biphenylyloxy)propyl]-4-(2-hydroxyethyl)piperazine dihydrochloride
33. 4-[3-(3-Chloro-2-biphenylyloxy)propyl]-1-(2-hydroxyethyl)piperazine dihydrochloride
34. N-Adamantyl-3-(2-biphenylylthio)propylamine hydrochloride
35. N-Adamantyl-4-(2-biphenylylthio)butylamine hydrochloride
36. 3-(2-Biphenylylthio)-N-cyclohexylpropylamine hydrochoride
37. N-Adamantyl-5-(5-chloro-2-biphenylyloxy)pentylamine hydrochloride
38. 4-(5-Chloro-2-biphenylyloxy)-N,N-diethylbutylamine hydrochloride
39. 3-(2-Chloro-5-biphenylyloxy)-N,N-diethylpropylamine hydrochloride
40. 4-(5-Chloro-2-biphenylyloxy)-di-n-butylamine hydrochloride
41. 4-(5-Chloro-2-biphenylyloxy)-N-cyclohexylbutylamine hydrochloride
42. 4-(5-Chloro-2-biphenylyloxy)-N,N-diisopropylbutylamine hydrochloride
43. 10-(5-Chloro-2-biphenylyloxy)-N,N-diethyldecylamine hydrochloride
44. 10-(5-Chloro-2-biphenylyloxy)-N-ethyl-N-(2-hydroxyethyl)decylamine hydrochloride
45. 3-(5-Chloro-2-biphenylylthio)-N-cyclohexylpropylamine hydrochloride
46. 10-(5-Chloro-2-biphenylyloxy)-N,N-dimethyldecylamine hydrochloride
47. 1-[3-(5-Chloro-2-biphenylyloxy)propyl]pyrrolidine
48. N-(t-Butyl)-3-(5-chloro-2-biphenylyloxy)propylamine
49. N-(n-Butyl)-3-(5-chloro-2-biphenylyloxy)propylamine
50. 3-(5-Chloro-2-biphenylyloxy)-N-phenylpropylamine hydrochloride
51. 3-(5-Chloro-2-biphenylyloxy)-3′-methoxy-di(n-propyl)amine
52. N-Benzyl-3-(5-chloro-2-biphenylyloxy)propylamine
53. 4-(5-Chloro-2-biphenylyloxy)-N-ethyl-N-(2-hydroxyethyl)butylamine hydrochloride
54. N-(n-Butyl)-3-(5-chloro-2-biphenylyloxy)-N-(2-hydroxyethyl)propylamine hydrochloride
55. 5-(5-Chloro-2-biphenylyloxy)-N-ethyl-N-(2-hydroxyethyl)pentylamine hydrochloride 56. 3-(3-Chloro-2-biphenylyloxy)-N,N,1-trimethylpropylamine hydrochloride
57. 6-(5-Chloro-2-biphenylyloxy)-N,N-dimethylhexylamine hydrochloride
58. 3-(5-Chloro-2-biphenylyloxy)-N-(2-hydroxyethyl)-N-methylpropylamine hydrochloride
59. N-(t-Butyl)-3-(2-chloro-4-biphenylyloxy)-propylamine hydrochloride
60. N-(t-Butyl)-5-(5-chloro-2-biphenylyloxy)-pentylamine hydrochloride
61. N-(t-Butyl)-6-(5-chloro-2-biphenylyloxy)hexylamine hydrochloride
62. 3-(2-Chloro-5-biphenylyloxy)-N-cyclohexylpropylamine hydrochloride The results of the test are recorded in Table 1, which follows. In the table, column 1 identifies the test compound by the number assigned to the compound in the list set forth hereinbefore; column 2, lists the application rate for each compound in parts per million (ppm.); and columns 3, 4 and 5 identify the test plants.

Table 1

| Compound No. | Appln. Rate ppm. | Hydrilla | Coontail | Duckweed |
|---|---|---|---|---|
| 1 | 10 | 5 | 5 | 3 |
|  | 1 | 1 | 1 | 2 |
| 2 | 10 | 5 | 5 | 5 |
|  | 1 | 1 | 3 | 1 |
| 3 | 10 | 5 | 5 | 3 |
|  | 1 | 1 | 2 | 1 |
| 4 | 10 | 3 | 5 | 2 |
|  | 1 | 2 | 2 | 1 |
| 5 | 10 | 5 | 5 | 4 |
|  | 4 | 5 | 5 | 1 |
|  | 2 | 4 | 5 | 2 |
|  | 1 | 2 | 2 | 3 |
|  | 0.5 | 2 | 4 | 1 |
| 6 | 10 | 5 | 5 | 5 |
|  | 4 | 5 | 4 | 5 |
|  | 2 | 1 | 2 | 5 |
|  | 1 | 2 | 5 | 2 |
| 7 | 10 | 5 | 5 | 5 |
|  | 4 | 5 | 3 | 5 |
|  | 2 | 4 | 4 | 4 |
|  | 1 | 3 | 4 | 2 |
|  | 0.5 | 1 | 1 | 2 |
| 8 | 10 | 2 | 5 | 2 |
|  | 1 | 1 | 2 | 1 |
| 9 | 10 | 4 | 5 | 4 |
|  | 1 | 3 | 2 | 1 |
| 10 | 10 | 4 | 5 | 1 |
|  | 1 | 1 | 4 | 1 |
| 11 | 10 | 5 | 5 | 5 |
|  | 1 | 3 | 1 | 1 |
| 12 | 10 | 5 | 5 | 3 |
|  | 1 | 4 | 1 | 1 |
| 13 | 10 | 2 | 5 | 3 |
|  | 1 | 1 | 5 | 1 |
| 14 | 10 | 5 | 5 | 1 |
|  | 1 | 3 | 4 | 1 |
| 15 | 10 | 5 | 5 | 5 |
|  | 4 | 5 | 5 | 5 |
|  | 2 | 4 | 2 | 3 |
|  | 1 | 2 | 3 | 1 |
|  | 0.5 | 1 | 1 | 1 |
| 16 | 10 | 5 | 5 | 4 |
|  | 1 | 1 | 3 | 1 |
| 17 | 10 | 5 | 5 | 5 |
|  | 4 | 5 | 5 | 5 |
|  | 2 | 3 | 3 | 4 |
|  | 1 | 2 | 4 | 2 |
|  | 0.5 | 2 | 1 | 1 |
| 18 | 10 | 2 | 5 | 1 |
|  | 1 | 4 | 2 | 1 |
| 19 | 10 | 4 | 5 | 4 |
|  | 1 | 4 | 1 | 1 |
| 20 | 10 | 5 | 5 | 4 |
|  | 1 | 3 | 2 | 1 |
| 21 | 10 | 4 | 5 | 4 |
|  | 1 | 3 | 2 | 1 |
| 22 | 10 | 5 | 5 | 5 |
|  | 4 | 5 | 3 | 5 |
|  | 2 | 1 | 1 | 2 |
|  | 1 | 3 | 3 | 1 |
| 23 | 10 | 5 | 5 | 4 |
|  | 4 | 3 | 4 | 4 |
|  | 2 | 1 | 1 | 2 |
|  | 1 | 3 | 5 | 2 |
| 24 | 10 | 5 | 5 | 5 |
|  | 4 | 4 | 4 | 5 |
|  | 2 | 2 | 4 | 4 |
|  | 1 | 3 | 4 | 2 |
|  | 0.5 | 3 | 1 | 2 |
| 25 | 10 | 5 | 5 | 4 |
|  | 5 | 5 | 5 | 4 |
|  | 1 | 4 | 5 | 2 |
|  | 0.1 | 1 | 4 | 1 |
| 26 | 10 | 5 | 5 | 5 |
|  | 5 | 5 | 5 | 5 |
|  | 4 | 4 | 4 | 4 |
|  | 2 | 3 | 4 | 3 |
|  | 1 | 3 | 4 | 2 |
|  | 0.5 | 2 | 1 | 1 |
| 27 | 10 | 5 | 5 | 5 |
|  | 5 | 5 | 5 | 4 |
|  | 1 | 2 | 4 | 2 |
|  | 0.1 | 1 | 4 | 3 |
| 28 | 10 | 5 | 5 | 5 |
|  | 4 | 4 | 4 | 5 |
|  | 2 | 1 | 1 | 2 |
|  | 1 | 4 | 5 | 1 |
| 29 | 10 | 5 | 5 | 5 |
|  | 5 | 5 | 5 | 5 |
|  | 1 | 3 | 5 | 2 |
|  | 0.5 | 2 | 4 | 1 |
| 30 | 10 | 2 | 5 | 2 |
|  | 1 | 4 | 1 | 1 |
| 31 | 10 | 5 | 5 | 1 |
|  | 1 | 1 | 5 | 1 |
| 32 | 10 | 4 | 5 | 4 |
|  | 1 | 1 | 2 | 1 |
| 33 | 10 | 4 | 5 | 1 |
|  | 1 | 1 | 1 | 2 |
| 34 | 10 | 5 | 5 | 2 |
|  | 1 | 5 | 4 | 1 |
| 35 | 10 | 4 | 5 | 4 |
|  | 1 | 3 | 4 | 1 |
| 36 | 10 | 5 | 5 | 2 |
|  | 1 | 1 | 3 | 1 |
| 37 | 10 | 4 | 5 | 1 |
|  | 1 | 1 | 2 | 1 |
| 38 | 10 | 5 | 5 | 4 |
|  | 4 | 3 | 5 | 1 |
|  | 2 | 2 | 2 | 1 |
| 39 | 10 | 5 | 5 | 1 |
|  | 1 | 3 | 2 | 1 |
| 40 | 10 | 5 | 5 | 4 |
|  | 4 | 4 | 5 | 1 |
|  | 2 | 2 | 3 | 1 |
| 41 | 10 | 5 | 5 | 3 |
|  | 4 | 4 | 5 | 3 |
|  | 2 | 5 | 5 | 3 |
|  | 1 | 3 | 4 | 2 |
|  | 0.5 | 3 | 3 | 2 |
| 42 | 10 | 5 | 5 | 4 |
|  | 4 | 2 | 4 | 4 |
|  | 2 | 1 | 2 | 3 |
|  | 1 | 3 | 5 | 1 |
| 43 | 10 | 3 | 5 | 2 |
|  | 1 | 3 | 1 | 1 |
| 44 | 10 | 4 | 5 | 1 |
|  | 1 | 2 | 3 | 1 |
| 45 | 10 | 5 | 5 | 2 |
|  | 1 | 3 | 5 | 1 |
| 46 | 10 | 4 | 5 | 3 |
|  | 4 | 3 | 5 | 1 |
|  | 2 | 2 | 2 | 1 |
| 47 | 10 | 5 | 5 | 4 |
|  | 4 | 4 | 5 | 1 |
|  | 2 | 3 | 3 | 1 |
| 48 | 10 | 5 | 5 | 4 |
|  | 4 | 5 | 5 | 1 |
|  | 2 | 4 | 5 | 2 |
|  | 1 | 1 | 4 | 3 |
|  | 0.5 | 1 | 4 | 1 |
| 49 | 10 | 5 | 5 | 4 |
|  | 4 | 5 | 5 | 1 |
|  | 2 | 4 | 5 | 2 |
|  | 1 | 2 | 4 | 3 |
|  | 0.5 | 1 | 1 | 1 |
| 50 | 10 | 3 | 1 | 1 |
|  | 1 | 3 | 1 | 1 |
| 51 | 10 | 5 | 5 | 4 |
|  | 4 | 5 | 5 | 2 |
|  | 2 | 5 | 5 | 2 |
|  | 1 | 3 | 5 | 4 |

Table 1-continued

| Compound No. | Appln. Rate ppm. | Hydrilla | Coontail | Duckweed |
|---|---|---|---|---|
|  | 0.5 | 2 | 4 | 2 |
| 52 | 10 | 5 | 5 | 4 |
|  | 4 | 4 | 5 | 1 |
|  | 2 | 4 | 5 | 2 |
|  | 1 | 2 | 5 | 1 |
|  | 0.5 | 1 | 5 | 1 |
| 53 | 10 | 5 | 5 | 5 |
|  | 4 | 1 | 4 | 4 |
|  | 2 | 1 | 4 | 2 |
|  | 1 | 2 | 5 | 1 |
| 54 | 10 | 5 | 5 | 4 |
|  | 1 | 2 | 5 | 2 |
| 55 | 10 | 5 | 5 | 2 |
|  | 5 | 5 | 5 | 4 |
|  | 1 | 3 | 5 | 2 |
|  | 0.1 | 1 | 2 | 1 |
| 56 | 10 | 2 | 4 | 4 |
| 57 | 10 | 5 | 5 | 4 |
|  | 4 | 4 | 3 | 3 |
|  | 2 | 1 | 3 | 1 |
|  | 1 | 2 | 5 | 3 |
| 58 | 10 | 5 | 5 | 5 |
|  | 1 | 1 | 1 | 1 |
| 59 | 10 | 4 | 5 | 4 |
|  | 4 | 4 | 4 | 3 |
|  | 2 | 3 | 3 | 2 |
| 60 | 10 | 5 | 5 | 4 |
|  | 4 | 5 | 5 | 2 |
|  | 2 | 3 | 3 | 2 |
| 61 | 10 | 5 | 5 | 2 |
|  | 4 | 4 | 4 | 3 |
|  | 2 | 4 | 4 | 3 |
|  | 1 | 5 | 5 | 3 |
|  | 0.5 | 3 | 4 | 2 |
| 62 | 10 | 5 | 5 | 5 |
|  | 4 | 5 | 5 | 3 |
|  | 2 | 4 | 4 | 3 |
|  | 1 | 3 | 5 | 3 |
|  | 0.5 | 1 | 1 | 2 |
| Control | 0 | 0 | 0 | 0 |

EXPERIMENT 2

In a second test, the number of plants used in the test was increased to a total of six, and the test was carried out as follows.

Four of the plants to be used in the test, namely Florida elodea, Southern Naiad, Eurasian milfoil, and Cabomba, were prepared by cutting four-inch terminal stems and burying the lower one inch of each stem in a mixture of sterilized sand-clay loam soil (50:50), in plastic 5-oz. drinking cups. The drinking cups containing the plants thus prepared were placed in 1-gallon wide-mouth jars two weeks prior to testing. Each jar was filled with water to the lower edge of the rim, the volume then being equal to approximately 3500 ml. of water. The water used was dechlorinated city water. There were then added to the top of the water in each jar a four-inch length of coontail, *Ceratophyllum demersum*, and approximately 60 duckweed plants, *Lemna minor* L. In addition, to promote the good growth of the plants, there was added to the water in each jar three drops of a mixture of 5 ml. chelated iron solution, 15 ml. water, and 15 ml. of a commercially available liquid fertilizer.

The following plants were used in this test:
Florida elodea, *Hydrilla verticillata* (L.F.)
Coontail, *Ceratophyllum demersum* (L.)
Duckweed, *Lemna minor* L.
Southern Naiad, *Najas quadalupensis* (Spreng.)
Eurasian milfoil, *Myriophyllum specatum* L.
Cabomba, *Cabomba caroliniana*, Gray At the end of 2 weeks, the jars containing healthy preconditioned plants were selected for testing.

The test compounds were formulated in the following manner. Twenty-seven mg. of compound was weighed into a 12 ml. disposable vial. To the vial containing the compound was added 1 ml. of acetone followed by 10 ml. of aqueous 0.1 percent polyoxyethylene sorbitan monooleate. This stock solution was then pipetted into the jars at volumes of 7.5, 3, 1.5, and 0.75 ml., to obtain 5, 2, 1, and 0.5 ppm. concentration of test compound in approximately 3500 ml. of water. Duplicates were run at each concentration of the compound. Controls to which no test compound was added were also run.

Herbicidal activity ratings were made each week for at least three weeks. The herbicidal activity rating was on a basis of 1–5, as was set forth in the description of Experiment 1 above.

The herbicidal activity ratings observed the third week of the experiment are recorded in Table 2, which follows.

Table 2

| Compound No. | Appln. Rate ppm. | Hydrilla | Coontail | Duckweed | Naiad | Milfoil | Cabomba |
|---|---|---|---|---|---|---|---|
| 5 | 2 | 5 | 5 | 4 | 5 | 5 | 5 |
|  | 1 | 3 | 5 | 3 | 5 | 4 | 4 |
|  | 0.5 | 3 | 5 | 1 | 3 | 5 | 4 |
| 7 | 2 | 5 | 5 | 5 | 5 | 5 | 5 |
|  | 1 | 5 | 5 | 5 | 3 | 5 | 4 |
|  | 0.5 | 2 | 3 | 2 | 1 | 5 | 2 |
| 15 | 2 | 2 | 1 | 1 | 1 | 2 | 2 |
|  | 1 | 1 | 1 | 1 | 1 | 2 | 4 |
|  | 0.5 | 1 | 1 | 1 | 1 | 1 | 2 |
| 17 | 2 | 5 | 5 | 5 | 5 | 4 | 3 |
|  | 1 | 4 | 5 | 5 | 2 | 5 | 2 |
|  | 0.5 | 1 | 3 | 2 | 2 | 2 | 2 |
| 24 | 2 | 5 | 5 | 5 | 5 | 5 | 5 |
|  | 1 | 4 | 5 | 4 | 3 | 5 | 4 |
|  | 0.5 | 4 | 5 | 2 | 2 | 5 | 5 |
| 25 | 5 | 5 | 5 | 5 | 5 | 5 | 5 |
|  | 1 | 5 | 5 | 4 | 5 | 5 | 5 |
|  | 0.1 | 1 | 5 | 2 | 2 | 3 | 1 |
| 26 | 2 | 5 | 5 | 5 | 5 | 5 | 5 |
|  | 1 | 4 | 5 | 5 | 5 | 5 | 4 |
|  | 0.5 | 3 | 5 | 4 | 2 | 5 | 4 |
| 27 | 5 | 5 | 5 | 5 | 5 | 5 | 5 |
|  | 1 | 4 | 5 | 3 | 5 | 5 | 4 |
|  | 0.1 | 1 | 4 | 2 | 3 | 2 | 3 |
| 29 | 5 | 5 | 5 | 5 | 5 | 5 | 5 |
|  | 1 | 2 | 5 | 4 | 2 | 5 | 4 |
|  | 0.1 | 3 | 5 | 2 | 4 | 4 | 2 |
| 41 | 2 | 5 | 5 | 5 | 4 | 5 | 5 |
|  | 1 | 4 | 5 | 4 | 3 | 5 | 5 |

Table 2-continued

| Compound No. | Appln. Rate ppm. | Hydrilla | Coontail | Duckweed | Naiad | Milfoil | Cabomba |
|---|---|---|---|---|---|---|---|
|    | 0.5 | 4 | 5 | 2 | 3 | 5 | 4 |
| 48 | 2   | 5 | 5 | 3 | 5 | 5 | 4 |
|    | 1   | 3 | 5 | 3 | 3 | 4 | 4 |
|    | 0.5 | 2 | 5 | 2 | 1 | 4 | 3 |
| 49 | 2   | 4 | 5 | 4 | 4 | 5 | 4 |
|    | 1   | 3 | 5 | 4 | 4 | 5 | 4 |
|    | 0.5 | 3 | 3 | 1 | 1 | 3 | 1 |
| 51 | 2   | 5 | 5 | 4 | 5 | 5 | 4 |
|    | 1   | 5 | 5 | 4 | 5 | 5 | 4 |
|    | 0.5 | 4 | 5 | 2 | 4 | 5 | 3 |
| 52 | 2   | 4 | 5 | 1 | 4 | 5 | 4 |
|    | 1   | 4 | 5 | 1 | 1 | 4 | 4 |
|    | 0.5 | 4 | 5 | 1 | 1 | 3 | 3 |
| 55 | 5   | 5 | 5 | 5 | 5 | 5 | 5 |
|    | 1   | 4 | 5 | 3 | 5 | 4 | 3 |
|    | 0.1 | 1 | 3 | 1 | 2 | 2 | 2 |
| 61 | 2   | 5 | 5 | 2 | 4 | 5 | 5 |
|    | 1   | 5 | 5 | 2 | 5 | 3 | 3 |
|    | 0.5 | 1 | 5 | 2 | 1 | 2 | 3 |
| 62 | 2   | 5 | 5 | 3 | 4 | 4 | 2 |
|    | 1   | 5 | 5 | 2 | 2 | 4 | 3 |
|    | 0.5 | 1 | 1 | 1 | 1 | 1 | 3 |
| Controls | 0 | 1 | 1 | 1 | 1 | 1 | 1 |

The tests show the practice of the novel method of this invention controls aquatic weeds.

I claim:

1. A method of destroying aquatic weeds in water which comprises contacting the weeds with an herbicidally-effective amount of a compound of the formula

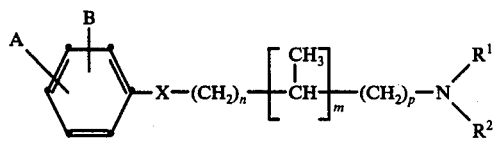

wherein
A is hydrogen, bromo, or chloro;
B is cyclohexyl, benzyl, or phenyl;
X is oxygen or sulfur;
$m$ is 0 or 1;
when $m = 0$, $n + p$ is 2 through 10; and
when $m = 1$, $n = p = 1$, or $n = 2$, $p = 0$;
$R^1$, when taken alone, is hydrogen, $C_1$-$C_5$ alkyl, or —$CH_2CH_2OH$;
$R^2$, when taken alone, is hydrogen, $C_1$-$C_5$ alkyl, $C_3$ alkenyl, cyclohexyl, —$CH_2CH_2OH$, —$(CH_2)_3OCH_3$, 1-adamantyl, or phenyl;
$R^1$ and $R^2$, when taken together with the nitrogen atom to which they are attached, form morpholino, 2-methylpiperidino, 4-(2-hydroxyethyl)piperazino, or pyrrolidino; and
the acid addition salts thereof.

2. The method of claim 1 wherein the active compound is of the formula

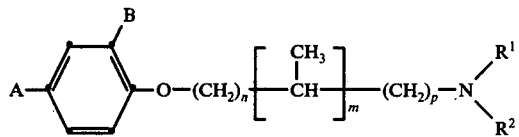

A is chloro;
B is phenyl;
$m$ is 0 or 1;
when $m = 0$, $n + p$ is 2 through 6; and
when $m = 1$, $n = p$ 32 1, or $n = 2$, and $p = 0$;
$R^1$ is hydrogen, $C_1$-$C_5$ alkyl, or -$CH_2CH_2OH$;
$R^2$ is hydrogen, $C_1$-$C_5$ alkyl, $C_3$ alkenyl, —$CH_2CH_2OH$, —$(CH_2)_3OCH_3$, or cyclohexyl; and
the acid addition salts thereof.

3. The method of claim 1 wherein the active compound is of the formula

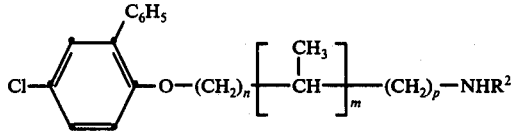

wherein
$m$ is 0 or 1;
when $m = 0$, $n + p$ is 2, 3, or 4;
when $m = 1$, $n = 2$, and $p = 0$;
$R^2$ is $C_2$—$C_4$ alkyl, cyclohexyl, or —$(CH_2)_3OCH_3$;
and the acid addition salts thereof.

4. The method of claim 1 wherein the herbicidally-effective amount of the active compound is from about 0.5 to about 10 ppm.

5. The method of claim 1 wherein the active compound is 3-(5-chloro-2-biphenylyloxy)-N-ethyl-1-methylpropylamine hydrochloride.

6. The method of claim 1 wherein the active compound is N-(t-butyl)-3-(5-chloro-2-biphenylyloxy)-propylamine hydrochloride.

7. The method of claim 1 wherein the active compound is 3-(5-chloro-2-biphenylyloxy)-N-isopropylpropylamine hydrochloride.

8. The method of claim 1 wherein the active compound is 3-(5-chloro-2-biphenylyloxy)-N-ethyl-N-(2-hydroxyethyl)propylamine hydrochloride.

9. The method of claim 1 wherein the active compound is 4-(5-chloro-2-biphenylyloxy)-N-cyclohexylbutylamine hydrochloride.

* * * * *

UNITED STATES PATENT OFFICE
CERTIFICATE OF CORRECTION

Patent No. 4,074,998   Dated February 21, 1978

Inventor(s) William B. Lacefield

It is certified that error appears in the above-identified patent and that said Letters Patent are hereby corrected as shown below:

Column 12, line 53: Change "hypochloride" to read --hypochlorite--.

Column 12, line 65: Change "5°" to read --15°--.

Column 32, line 21: A new paragraph should begin at --At the end of 2--.

Column 34, line 26: Change "p32 1" to read --p = 1--.

Please note between the empirical formula of the base compound and the empirical formula of the acid which forms the salt with the base compound, the period should be positioned in the middle of the height of the letters instead of on the line at the following locations:

Column 12, line 26;
Column 15, line 6;
Column 15, line 36;
Column 15, line 49;
Column 15, line 62;
Column 16, line 8;
Column 16, line 50;
Column 17, line 15;
Column 17, line 30;
Column 17, line 68;
Column 18, line 17;
Column 18, line 30;
Column 18, line 43;
Column 18, line 57;
Column 19, line 5;

UNITED STATES PATENT OFFICE
CERTIFICATE OF CORRECTION

Patent No. 4,074,998              Dated February 21, 1978

Inventor(s) William B. Lacefield

It is certified that error appears in the above-identified patent and that said Letters Patent are hereby corrected as shown below:

```
Column 19, line 19;
Column 19, line 32;
Column 19, line 45;
Column 19, line 58;
Column 20, line 15;
Column 20, line 28;
Column 20, line 41;
Column 20, line 55;
Column 20, line 68;
Column 21, line 14;
Column 21, line 28;
Column 21, line 41;
Column 21, line 54;
Column 21, line 68;
Column 22, line 28;
Column 22, line 48;
Column 22, line 61;
Column 24, line  8;
Column 24, line 21;
Column 24, line 34;
Column 24, line 48;
Column 24, line 62;
```

UNITED STATES PATENT OFFICE
CERTIFICATE OF CORRECTION

Patent No. 4,074,998           Dated February 21, 1978

Inventor(s) William B. Lacefield

It is certified that error appears in the above-identified patent and that said Letters Patent are hereby corrected as shown below:

Column 25, line 15;
        Column 25, line 33;
        Column 25, line 48;
        Column 25, line 63.

Signed and Sealed this

Twenty-seventh Day of June 1978

[SEAL]

Attest:

RUTH C. MASON
*Attesting Officer*

DONALD W. BANNER
*Commissioner of Patents and Trademarks*